United States Patent
Eggink et al.

(10) Patent No.: US 9,155,796 B2
(45) Date of Patent: Oct. 13, 2015

(54) HYDROGELS WITH COVALENTLY LINKED POLYPEPTIDES

(71) Applicant: SUSAVION BIOSCIENCES, INC., Tempe, AZ (US)

(72) Inventors: Laura L. Eggink, Scottsdale, AZ (US); J. Kenneth Hoober, Phoenix, AZ (US)

(73) Assignee: Susavion Biosciences, Inc., Tempe, AZ (US)

( * ) Notice: Subject to any disclaimer, the term of this patent is extended or adjusted under 35 U.S.C. 154(b) by 0 days.

(21) Appl. No.: 14/097,215

(22) Filed: Dec. 4, 2013

(65) Prior Publication Data
US 2014/0155313 A1    Jun. 5, 2014

Related U.S. Application Data

(60) Provisional application No. 61/733,403, filed on Dec. 4, 2012.

(51) Int. Cl.
*A61K 9/00* (2006.01)
*A61K 38/08* (2006.01)
*A61L 15/32* (2006.01)
*C07K 1/113* (2006.01)
*A61K 47/48* (2006.01)
*A61K 38/02* (2006.01)

(52) U.S. Cl.
CPC ............ *A61K 47/48176* (2013.01); *A61K 38/02* (2013.01); *A61K 38/08* (2013.01); *A61K 47/48784* (2013.01); *A61L 15/32* (2013.01); *C07K 1/1133* (2013.01)

(58) Field of Classification Search
None
See application file for complete search history.

(56) References Cited

U.S. PATENT DOCUMENTS

| | | | |
|---|---|---|---|
| 2005/0208469 A1* | 9/2005 | Daunert et al. | 435/4 |
| 2009/0130756 A1* | 5/2009 | Klann et al. | 435/374 |
| 2012/0178913 A1* | 7/2012 | Lin et al. | 530/410 |

* cited by examiner

*Primary Examiner* — Jeffrey E Russel
(74) *Attorney, Agent, or Firm* — Rodney J. Fuller; Booth Udall Fuller, PLC

(57) ABSTRACT

The present invention provides methods of synthesizing hydrogels that contain covalently linked polypeptides. These polypeptides may be tetravalent peptides or polypeptides that bind to cell surface receptors. The hydrogels synthesized by the methods of the present invention may be used in wound dressings or applied directly to wounds to promote healing.

13 Claims, 2 Drawing Sheets

3-Iodo-2-methyl-1-propene

HYDROGELS WITH COVALENTLY LINKED POLYPEPTIDES

CROSS-REFERENCE TO RELATED APPLICATIONS

This application claims the benefit of U.S. Provisional Application No. 61/733,403, filed Dec. 4, 2012, the contents of which are incorporated herein by reference in its entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 1,037 byte ASCII (text) file named "Seq_List" created on Dec. 4, 2013.

TECHNICAL FIELD

This application relates to hydrogels in which polypeptides have been covalently linked to the polymeric scaffold, methods of synthesizing the hydrogels, and use of the hydrogels to deliver drugs or other biologically-active agents to a subject in need thereof. This application also relates to devices, such as wound dressings, incorporating the hydrogels.

BACKGROUND

Hydrogels consist of a three-dimensional, polymeric network that holds a liquid medium and retains it through surface tension effects. The network of polymer chains is hydrophilic and can contain over 99.9% water. Hydrogels also possess a degree of flexibility very similar to natural tissue because of their significant water content. These gels have no known toxicity and have been approved for clinical use. Common uses for hydrogels include scaffolds in tissue engineering. When used as scaffolds, hydrogels may contain human cells to repair tissue; hydrogel-coated wells used for cell culture; environmentally sensitive hydrogels, known as 'Smart Gels' or 'Intelligent Gels,' have the ability to sense changes of pH, temperature, or concentration of metabolites and release their load as result of such a change; sustained-release drug delivery systems; absorption and debriding of necrotic and fibrotic tissue; biosensors formed from hydrogels that are responsive to specific molecules, such as glucose or antigens; absorbents in disposable diapers where they absorb urine, or in sanitary napkins; contact lenses (silicone hydrogels, polyacrylamides); EEG and ECG medical electrodes using hydrogels composed of cross-linked polymers (polyethylene oxide, polyAMPS and polyvinylpyrrolidone); water gel explosives; and rectal drug delivery and diagnosis. Other, less common uses include breast implants; glue; granules for holding soil moisture in arid areas; dressings for healing of burn or other hard-to-heal wounds (which are excellent for helping to create or maintain a moist environment); and reservoirs in topical drug delivery—particularly ionic drugs, delivered by ionophoresis.

Advantageous properties and uses of hydrogels may be extended by incorporation of copolymer substrates. For example, addition of polypeptides to a hydrogel could provide a variety of surface properties to the polymer. There is a need in the field to provide effective ways of chemically linking polypeptides to hydrogels to provide mechanically stable compositions.

SUMMARY

The present invention provides a composition comprising an acrylate polymeric scaffold covalently linked to a compound represented by formula (II):

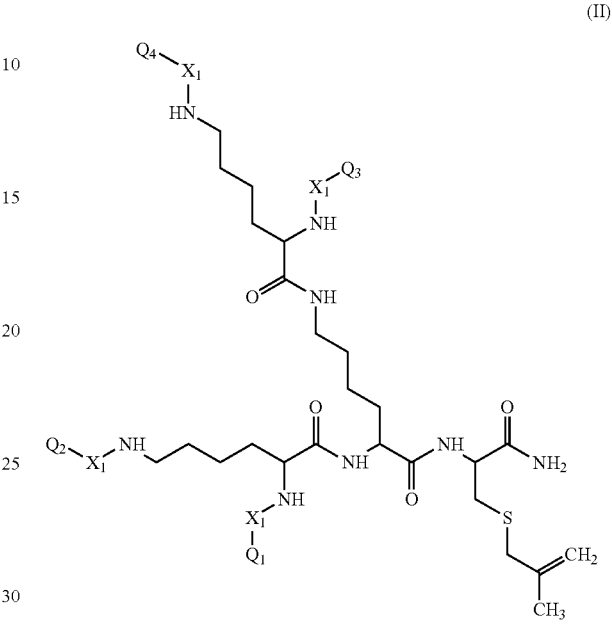

wherein $X^1$ is a linker selected from the group consisting of polyethylene glycol (PEG) and an amino acid sequence consisting of GGGS (SEQ ID NO: 1), and each of $Q^1$, $Q^2$, $Q^3$, and $Q^4$ is independently a therapeutic polypeptide.

In certain aspects, the acrylate polymeric scaffold is covalently linked to the compound represented by formula (II) at the vinyl group on the C-terminal cysteinyl amide. The acrylate polymeric scaffold may comprise an acrylate selected from any one of the following: 2-Hydroxyethyl Methacrylate, Methyl Methacrylate, Hydroxymethacrylate, Hydroxy Ethyl Meth Acrylate (HEMA), Poly Glucosylethyl Methacrylate (PGEMA), Poly Ethyl Methacrylate (PEMA), and Poly Methyl Methacrylate (PMMA).

In other embodiments, $Q^1$, $Q^2$, $Q^3$ and $Q^4$ may be a full-length polypeptide or an active peptide fragment of a polypeptide selected from the group consisting of cytokines, growth factors, cell adhesion molecules, and antibodies. In certain aspects, each of $Q^1$, $Q^2$, $Q^3$, and $Q^4$ independently comprises an amino acid sequence selected from the group consisting of SEQ ID NO: 2, SEQ ID NO: 3, SEQ ID NO: 4, and SEQ ID NO: 5.

The present invention also provides a method by which polypeptides are derivatized to form a copolymer substrate for incorporation into a hydrogel. In some embodiments, the polypeptides are full-length or active peptide fragments of cytokines, growth factors, cell adhesion molecules or antibodies. The polypeptides may also be tetravalent peptides such as SVH1B, SV6D, SVD2, and SVC1 as described herein.

Because the polypeptides are covalently linked to the hydrogel, it is advantageous for the polypeptides to have an effect at the cell surface. In a preferred embodiment, the polypeptides of the present invention bind to and activate cell surface receptors. In one aspect of the invention, the polypeptides have a molecular weight of less than 200 kD.

In some embodiments, the hydrogels of the present invention contain pharmacologically-active agents in addition to the polypeptides linked to the hydrogel scaffold. The pharmacologically-active agents may be vulnerary agents, hemostatic agents, antibiotics, antihelminthics, anti-fungal agents, hormones, anti-inflammatory agents, polypeptides, oligonucleotides, cytokines, antibodies, enzymes or any combination of these agents.

In another aspect, the present invention is directed to hydrogels produced by the methods disclosed. These hydrogels may be used in wound dressings or as a treatment for a wound in a subject.

DETAILED DESCRIPTION

Figure 1:
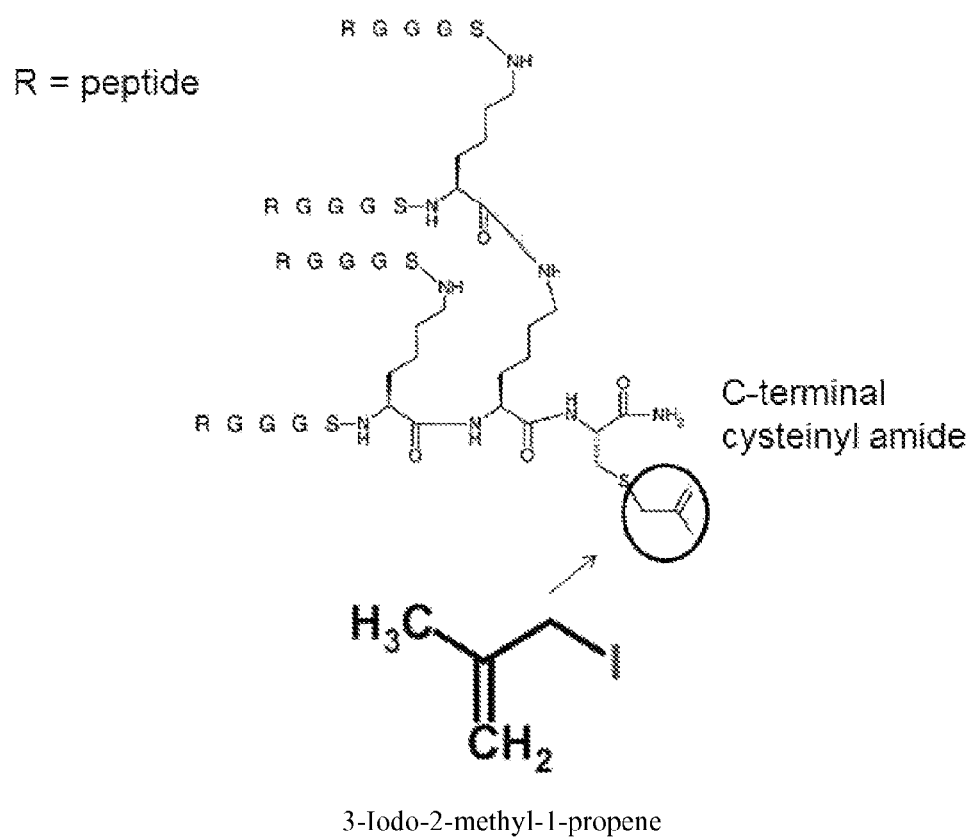
FIG. 1 depicts a structural scheme of a tetravalent peptide with a C-terminal cysteine attached to 2-methyl-1-propene. Addition of the vinyl group can be accomplished with 3-iodo-2-methyl-1-propene or allyl-iodide, which lacks the methyl group of 3-iodo-2-methyl-1-propene. The R groups shown represent active peptide sequences.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

The term "hydrogel" (also called aquagel) refers to a network of oligomers or polymer chains that are water-insoluble, sometimes found as a colloidal gel in which water is the dispersion medium. Hydrogels are natural or synthetic polymers that show superabsorbent properties (having even over 99% water). Hydrogels also possess a degree of flexibility very similar to natural tissue, due to their significant water content.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, polypeptides include natural peptides, recombinant peptides, synthetic peptides or a combination thereof. A peptide that is not cyclic has an N-terminus and a C-terminus The N-terminus has an amino group, which may be free (i.e., as a $NH_2$ group) or appropriately protected (for example, with a BOC or a Fmoc group or acetate). The C-terminus has a carboxylic group, which may be free (i.e., as a COOH group) or appropriately protected (for example, as a benzyl or a methyl ester or an amide). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

As used herein, the terms "entrain" and "entrainment" refer to the entrapment of one substance by another substance. This entrapment may be reversible. For example, a pharmacologically-active agent may be entrained in a hydrogel and later released when the hydrogel is applied to a biological surface such as a wound.

As used herein, the term "alkyl" refers to hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

As used herein, the term "aryl" refers to an aromatic hydrocarbon radical derived by the removal of one hydrogen atom from a single carbon atom of a parent aromatic ring system. For example, an aryl group can have 1 to 20 carbon atoms, 1 to 4 carbon atoms, 4 to 20 carbon atoms, 4 to 18 carbon atoms, 4 to 16 carbon atoms, 4 to 14 carbon atoms, 4 to 12 carbon atoms, 4 to 10 carbon atoms, 4 to 8 carbon atoms, or 4 to 6 carbon atoms. Typical aryl groups include, but are not limited to, radicals derived from benzene (e.g., phenyl), substituted benzene, naphthalene, anthracene, biphenyl, and the like.

As used herein, the term "substituted alkyl" means alkyl in which one or more hydrogen atoms are each independently replaced with a non-hydrogen substituent.

As used herein, the term "heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or a thioalkyl group (e.g., —$SCH_3$). A heteroalkyl group can have, for example, 1 to 20 carbon atoms, 1 to 4 carbon atoms, 4 to 20 carbon atoms, 4 to 18 carbon atoms, 4 to 16 carbon atoms, 4 to 14 carbon atoms, 4 to 12 carbon atoms, 4 to 10 carbon atoms, 4 to 8 carbon atoms, or 4 to 6 carbon atoms. A $C_1$-$C_6$ heteroalkyl group means a heteroalkyl group having 1 to 6 carbon atoms.

Hydrogel Compositions

Polymeric scaffolds are attractive vehicles to introduce drugs into tissues and for microengineering tissue reconstruction. The scaffolds are often formed from acrylate polymers, which are formed by a polymerization chain reaction of derivatives of acrylic acid. A radical initiator starts a chain reaction ultimately forming an alkane chain composed of carbons from the vinyl group of the monomer. For example, the vinyl group of acrylic acid reacts with a radical initiator and then reacts with the vinyl group of another molecule of acrylic acid, which then proceeds by a chain reaction to other acrylic acid molecules to form the polymeric backbone. Common acrylic acid derivatives include esters formed with addition of an alcohol and addition of a methyl group on carbon-2. Other compounds that may be used to generate the scaffold of the hydrogels of the present invention are shown in Table 1 and include 2-hydroxyethyl methacrylate, methyl methacrylate, 2-acrylamido-2-methylpropane sulfonic acid (AMPS), and hydroxymethacrylate.

TABLE 1

Hydrophilic polymers used in preparation of hydrogels.

| Natural polymers and their derivatives | Anionic polymers | HA, alginic acid, pectin, carrageenan chondriotin sulfate, dextran sulfate |
| --- | --- | --- |
| | Cationic polymers | chitosan, polysine |
| | Amphipathic polymers | collagen (and gelatin), carboxymethyl chitin, fibrin |
| | Neutral polymers | dextran, agarose, pullulan |
| Synthetic polymers | Polyesters | PEG-PLA-PEG, PEG-PLGA-PEG, PEG-PCL-PEG, PLA-PEG-PLA, PHB, P(PF-co-EG)6acrylate end groups, P(PEG/PBO terephthalate) |
| | Other polymers | PEG-bis-(PLA-acrylate), PEG6CDs, PEG-g-P(AAm-co-Vamine), PAAm, P(NIPAAm-co-AAc), P(NIPAAm-co-EMA), PVAc/PVA, PNVP. P(MMA-co-HEMA), P(AN-coallyl sulfonate), P(biscarboxy-phenoxy-phosphazene), P(GEMA-sulfate). |
| Combinations of natural and synthetic polymers | | P(PEG-co-peptides), alginate-g-(PEO-PPO-PEO). P(PLGA-co-serine), collagen-acrylate, alginate-acrylate, P(HPMA-g-peptide), P(HEMA/Matrigel ®), HA-g-NIPAAm. |

Abbreviations Used in Table 1:

HA (Hyaluronic Acid); PEG (Poly Ethylene Glycol); PLA (Poly Lactic Acid); PLGA (Poly Lactic-co-Glycolic Acid); PCL (Poly Capro Lactone; PHB (Poly Hydroxyl Butyrate); PF (Propylene Fumarate); EG (Ethylene Glycol); PBO (Poly Butylene Oxide); CD (Cyclo Dextrin); PAAm (Polyacrylamide); PNIPAAm (Poly N-isopropyl Acrylamide); PVA (Poly Vinyl Alcohol); PVamine (Poly Vinyl amine); PVAc (Poly Vinyl Acetate); PNVP (Poly N-vinyl Pyrrolidone); PAAc (Poly Acrylic Acid); HEMA (Hydroxy Ethyl Meth Acrylate); PAN (Polyacrylonitrile); PGEMA (Poly Glucosylethyl Methacrylate); PEO (Poly Ethylene Oxide); PPO (Poly Propyleneoxide); PHPMA (Poly hydroxypropyl methacrylamide); PEMA (Poly ethyl methacrylate); PAN (Polyacrylonitrile); PMMA (Poly methyl methacrylate). See Patel et al., American Journal of PharmTech Research. 2011; 1(3):19-38.

Examples of radical initiators that may be used with the present invention are halogen molecules (e.g., $Cl_2$), azo compounds (e.g., AIBN and ABCN), and organic peroxides (e.g., di-tert-butyl peroxide, benzoyl peroxide, methyl ethyl ketone peroxide, dilauroyl peroxide (LPO), and acetone peroxide), riboflavin, and ammonium persulfate.

Additional ingredients that may be used in the hydrogels of the present invention are, for example, polyvinyl alcohol, sodium polyacrylate, and acrylate polymers with an abundance of hydrophilic groups. Natural hydrogel materials may also be used in the present invention for tissue engineering; these materials include agarose, methylcellulose, hyaluronan, and other naturally derived polymers.

The hydrogels of the present invention may be composed of two or more copolymers. In some embodiments, the hydrogel is synthesized with a first peptide polymer that comprises a C-terminal cysteine sulfhydryl group, which reacts with a halogen on a compound represented by formula (I):

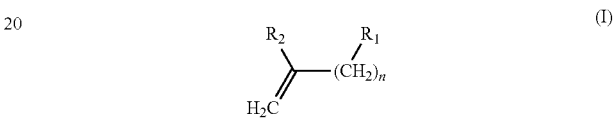

wherein $R_1$ represents a halogen and $R_2$ represents an alkyl or a substituted alkyl. In some embodiments, $R_2$ represents a methyl, an ethyl, a hydroxymethyl, a hydroxyethyl, or a hydrogen. In certain embodiments, n in formula (I) is an integer between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 1 and 4, between 1 and 3, or between 1 and 2. The reaction between the first peptide polymer and the compound of formula (I) introduces a vinyl group onto the first peptide polymer as shown in FIG. 1. Non-limiting examples of compounds represented by formula (I) that may be used in the present invention are 3-iodo-2-methyl-1-propene and allyl-idodide. Once the vinyl group has been added to the first peptide polymer, the first peptide polymer is added to a second polymer with a radical initiator to begin polymerization of the hydrogel.

In some embodiments, the first peptide polymer in the hydrogel is a polypeptide. Polypeptides used in the present invention may bind cell surface receptors and include full-length and active peptide fragments of cytokines, growth factors, cell adhesion molecules, and antibodies. An "active peptide fragment" of a cytokine, growth factor, cell adhesion molecule or antibody is a peptide that contains amino acid residues that bind to a cell surface receptor and trigger intracellular events.

In certain embodiments, antibodies or their active peptide fragments are derivatized and covalently linked to the hydrogel scaffold and afterwards coupled with therapeutic polypeptides.

In another aspect of the invention, the first peptide polymer in the hydrogel is a tetravalent peptide. U.S. Pat. No. 7,838, 497 to Eggink and Hoober describes several peptides that stimulate release of pro-angiogenic cytokines in cultures of peripheral blood mononuclear cells (PBMCs). Major pro-angiogenic cytokines are PDGF and its homolog VEGF. In these cultures, tetravalent peptides designated SVH1B, SV6D, SVD2 and SVC1 stimulated increased PDGF secretion two- to four-fold within 4 hours. The sequences of SVH1B, SV6D, SVD2 and SVC1 are shown in Table 2. SVH1B, SV6D, SVD2, and SVC1 contain the therapeutic peptides of sequences WNSTL (SEQ ID NO: 2), NQHTPR (SEQ ID NO: 3), VSNQH (SEQ ID NO: 4), and VQATQS (SEQ ID NO: 5), respectively.

TABLE 2

Sequences of exemplary tetravalent peptides that can be used with the present invention. The first capital letters in each sequence are the standard one-letter abbreviations for the natural amino acids. PEG2: (polyethylene glycol)$_2$ linker; Lys: lysine; Cys[—CH2CH(Me): CH2]—NH2: 2-methyl-1-propene adduct on a C-terminal cysteinyl amide.

| | |
|---|---|
| SVH18 | (WNSTL-PEG2-)4-Lys2-Lys-PEG2-Cys[CH2CH(Me): CH2]—NH2 |
| SV6D | (NQHTPR-PEG2-)4-Lys2-Lys-PEG2-Cys[—CH2CH(Me): CH2]—NH2 |
| SVD2 | (VSNQH-PEG2-)4-Lys2-Lys-PEG2-Cys[—CH2CH(Me): CH2]—NH2 |
| SVC1 | (VQATQS-PEG2-)4-Lys2-Lys-PEG2-Cys[—CH2CH(Me): CH2]—NH2 |

The polypeptides used in the hydrogels of the present invention may be of various molecular weights. In some embodiments, the polypeptides of the present invention have a molecular weight that is less than 800 kilodaltons (kD), less than 750 kD, less than 700 kD, less than 650 kD, less than 600 kD, less than 550 kD, less than 500 kD, less than 450 kD, less than 400 kD, less than 350 kD, less than 300 kD, less than 250 kD, less than 200 kD, less than 150 kD, less than 100 kD, less than 90 kD, less than 80 kD, less than 70 kD, less than 60 kD, less than 50 kD, less than 40 kD, less than 30 kD, less than 20 kD, or less than 10 kD.

In some embodiments, a pharmacologically-active agent is added to the hydrogel. Any pharmacologically-active agent, without limitation, can be incorporated into the hydrogels of the present invention, including (by way of illustration and not limitation) vulnerary agents, hemostatic agents, antibiotics, antithelmintics, anti-fungal agents, hormones, anti-inflammatory agents, polypeptides, oligonucleotides, cytokines, antibodies, and enzymes. These pharmacologically-active agents may be incorporated into the hydrogel before the polymerization of the hydrogel, during the polymerization of the hydrogel, or after the polymerization has terminated. In a preferred embodiment, the pharmacologically-active agent is added after polymerization is terminated.

Likewise, all of the hydrogels according to the present invention may further comprise living cells entrained within the hydrogel. The entrained cells may be stem cells or differentiated somatic cells. Hydrogels containing entrained living cells may be used in tissue engineering.

Methods of Using the Hydrogel Compositions

The hydrogels of the present invention find many uses, one of which is as a functional wound dressing. The hydrogels of the present invention may be incorporated into bandages, surgical and dental wound packing material, and the like.

The novel hydrogel constructs described herein are not physical blends, which are common in the formulation of current biomedical hydrogels; hence, the chemical and physical properties of the subject hydrogels are homogenous and can be tailored to suit a particular clinical end-point requirement. Furthermore, the hydrogel constructs are mechanically stable because the components are covalently bonded. In addition, the hydrophilicity and flexibility of the porous hydrogels accommodate the absorption of wound exudate and assist the final removal of the material from the wound site. The nature and the porosity of the construct further facilitate the exchange of gases and allow healing. Most importantly, the presence of covalently-linked bioactive peptides and the potential loading of other pharmaceutical compounds within the matrix allows for the temporally- and spatially-controlled delivery of bioactive signals to modulate and complement the dynamics of the host healing process.

The present invention offers several key commercial advantages over existing products. For example, despite the extensive investigation in the development of novel wound dressing materials, very few materials are used clinically due to the multiple requirements necessary for a functional wound dressing. Ideal functional wound dressings must be nontoxic, biocompatible, permeable to moisture and gases to absorb wound exudate and toxins, as well as to maintain humidity and oxygen levels. The dressings should be porous to prevent swelling of the wound bed and to prevent accumulation of fluid between the wound site and the material. They should be flexible and durable. They should be biocompatible and minimize local inflammation and infection. They should promote neovascularization, re-epithelialization, and normal healing. The novel multi-functional hydrogels described herein can be made to address all of the above requirements for a clinically viable wound dressing material.

The hydrogels of the present invention can also be used in any application where hydrogels are currently employed. Thus, the hydrogels of the present invention find use as wound dressings, diapers, catamenial devices, and the like. In one embodiment, the hydrogels are used to administer a pharmacologically-active agent to a patient in need of the pharmacologically-active agent. In this use, the pharmacologically-active agent either is covalently bonded within the gel or entrained within the gel. In a preferred embodiment, the pharmacologically-active agent is entrained within the gel. The gel is then administered to the patient, as by packing it into a surgical or traumatic wound. The polypeptides covalently linked to the hydrogel scaffold may also be therapeutic and promote healing by reducing inflammation, for example.

The hydrogels of the present invention are also useful as scaffolds to support living cells. Thus, the hydrogels of the present invention can be used as biomechanical devices. The hydrogels will support living cells within the bulk of the gel, thereby providing a three-dimensional support network in which the cells can grow and proliferate. Hydrogels according to the present invention that contain cells can be implanted into a patient in need of such cells.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1

Synthesis of Polypeptide Copolymers for Incorporation into Hydrogels

The peptides were synthesized as either monomeric or multivalent molecules with the sequences extending from the four amino groups of a tri-lysine core, i.e., [active sequence-linker-K]2K2K-linker-C-NH2 as shown in FIG. 1. The linker may be composed of polyethylene glycol (PEG) or a short amino acid sequence as GGGS (SEQ ID NO:1). For incorporation into the scaffold of a hydrogel polymer, the sulfhydryl group of the C-terminal cysteine was reacted with 3-iodo-2-methyl-1-propene to add a vinyl group. This vinyl group reacts with other vinyl groups of the copolymer during the polymerization chain reaction, which then covalently links the peptide into the hydrogel. An alternate reagent to add the vinyl group is allyl-iodide. The linker referred to above may also extend the active sequence (represented as "R" in FIG. 1) away from the tri-lysine core and also the complete peptide away from the matrix of the polymer. To prevent photodynamic oxidation of sensitive side chains of amino acids in the active peptide sequences, photopolymerization is done in the absence of oxygen.

Figure 2:
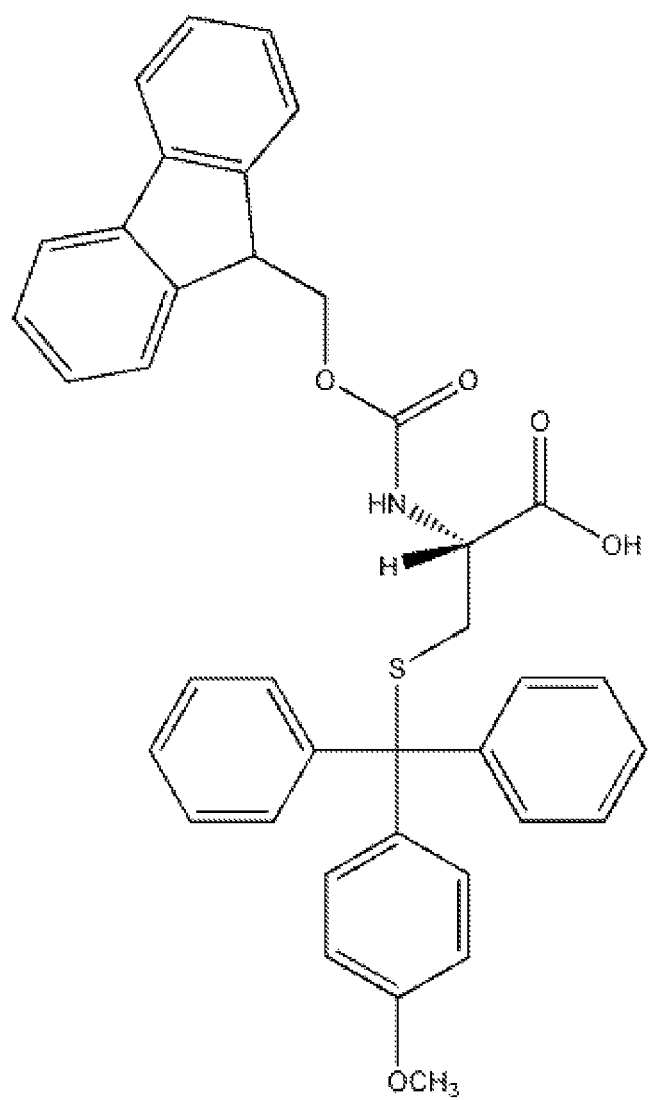
FIG. 2 depicts the structure of N-alpha-(9-Fluorenylmethyloxycarbonyl)-S-p-methoxytrityl-L-cysteine (Fmoc-L-Cys(Mmt)-OH) used in the synthesis of the tetravalent peptides of the present invention.

Tetravalent peptides were synthesized by standard chemistry utilizing Fmoc (9-fluorenylmethoxycarbonyl)-protected amino acids. FIG. 2 shows the compound Fmoc-L-Cys (Mmt)-OH (also known as Fmoc-Cys(4-methoxytrityl)-OH, N-alpha-(9-Fluorenylmethyloxycarbonyl)-S-p-methoxytrityl-L-cysteine, N-α-Fmoc-S-ρ-methoxytrityl-L-cysteine, and N-α-Fmoc-S-4-methoxytrityl-L-cysteine), which is used to protect amino acids and has a molecular formula of $C_{38}H_{33}NO_5S$ and Chemical Abstracts Service (CAS) Number 177582-21-7.

Synthesis of the peptides was initiated with Fmoc-L-Cys (Mmt)-OH attached to a resin that leads to a C-terminal amide group when the peptide is cleaved from the resin. The protocol for the use of this derivative (i.e., Fmoc-L-Cys(Mmt)-OH) in solid-phase peptide synthesis is described by CBL Biopharma, Patras, Greece and in Vasileiou Z, et al., 2009, "Convergent solid-phase and solution approaches in the synthesis of the cysteine-rich Mdm2 RING finger domain," *J Pept Sci* 15:824-831. The S-Mmt function was cleaved selectively by acid in the presence of t-butyl type protecting groups and the 4-methyl benzhydryl resin, the Wang resin or the Rink amide MBHA resin. The highly acid labile S-Mmt group is preferred over the S-tBu group. The liberated thiol function is ready to then selectively react with various compounds, such as haloacylated or haloalkylated derivatives, among others.

Protecting groups for amino acid side chains during synthesis were tert-butyl for the hydroxyl group of serine, Boc (tert-butyloxycarbonyl) for the ε-amino group of lysine, PBF (2,2,4,6,7-pentamethyl-2,3-dihydrobenzofuran-5-sulfonyl) for arginine, or trityl for the imidazole group of histidine. The most difficult blocking groups to remove were tert-butyl (56 Da) and PBF (253 Da). The blocking groups were removed by trifluoroacetic acid (TFA) during cleavage of the peptide from the resin after synthesis. The peptide was dried, dissolved in water, neutralized and mixed with a buffering compound that maintained a pH between 7 and 8. Iodo-compounds such as 3-iodo-2-methyl-1-propene were dissolved in dimethyl sulfoxide, methanol or another suitable organic solvent and allowed to react with the sulfhydryl group for an hour at room temperature. The resulting peptide was purified by HPLC with an acetonitrile gradient in water containing 0.1% TFA. The peptide was again dried, dissolved in water, neutralized. The final peptide was ready to be added to a hydrogel polymerization mixture.

Example 2

Photopolymerization of Substituted Acrylates

Covalent incorporation of the peptides into the hydrogel during polymerization requires the absence of oxygen to prevent (photo)oxidation of sensitive amino acid side chains, specifically of the amino acids tryptophan and histidine. The protocol for hydrogel formation must therefore accommodate this issue.

Photopolymerization of substituted acrylates has been extensively reported in the literature. The formation of the polymer will require a co-initiator, usually a tertiary amine, and will proceed via free radical polymerization. See Encinas, et al., 2001, "Free radical polymerization photoinitiated by riboflavin/amines Effect of the amine structure," *Macromolecules* 34:2845-2847. The reaction will be inhibited by any element or compound such as oxygen that serves as a free radical trap. Therefore, one of the most important steps in the preparation of the hydrogels will be the evacuation, or "degassing" of gel solutions immediately prior to polymerization.

The conversion of riboflavin from the flavo to the leuco form (the species active in initiation) actually requires a small amount of oxygen. Thus, because elimination of oxygen from the system is essential, riboflavin will not be a suitable initiator because polymerization initiated primarily by riboflavin can be completely blocked by exhaustive degassing. Other photosensitizers have been described in the literature such as camphorquinone (Cook, 1992, "Photopolymerization kinetics of dimethacrylates using camphorquinone/amide initiator system," *Polymer* 33:600-609) and 4-n-propoxythioxanthone (Allen et al., 1988, "Spectroscopic properties and photopolymerization activity of 4-n-propoxythioxanthone," *European Polymer Journal* 24:435-440) that are not sensitive to the absence of oxygen. Means of initiating polymerization continue to be an intensely studied area of research, and other photosensitizers besides those listed here will be of use in the initiation of polymerization.

The contents of all references, patents, and published patent applications cited throughout this application, as well as the Figures, are incorporated herein by reference in their entirety for all purposes.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of synthesizing a hydrogel comprising:
   (a) reacting a C-terminal cysteine sulfhydryl group of a polypeptide with a halogen on a compound represented by formula (I):

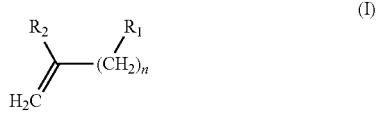

wherein n is an integer between 1 and 6, $R_1$ represents a halogen, and $R_2$ represents a methyl, an ethyl, a hydroxymethyl, a hydroxyethyl, or a hydrogen; and
   (b) adding the reacted polypeptide to an acrylic acid derivative with a radical initiator to begin polymerization of the hydrogel.

2. The method of claim 1, wherein the polypeptide is incorporated into a tetravalent structure.

3. The method of claim 2, wherein the polypeptide is selected from the group consisting of WNSTL (SEQ ID NO: 2), NQHTPR (SEQ ID NO: 3), VSNQH (SEQ ID NO: 4), and VQATQS (SEQ ID NO: 5).

4. The method of claim 1, wherein the polypeptide binds to cell surface receptors.

5. The method of claim 4, wherein the polypeptide is a full-length polypeptide or an active peptide fragment of a polypeptide selected from the group consisting of cytokines, growth factors, cell adhesion molecules, and antibodies.

6. The method of claim 1, wherein the polypeptide has a molecular weight of less than 200 kilodaltons (kD).

7. The method of claim 1, wherein the compound represented by formula (I) is selected from the group consisting of 3-iodo-2-methyl-1-propene and allyl-iodide.

8. The method of claim 1, wherein the acrylic acid derivative is selected from the group consisting of acrylic acid, 2-hydroxyethyl methacrylate, methyl methacrylate, 2-acrylamido-2-methylpropane sulfonic acid (AMPS), and hydroxymethacrylate.

9. The method of claim 1, further comprising:
   (c) adding a pharmacologically-active agent to the hydrogel after polymerization is terminated.

10. The method of claim 9, wherein the pharmacologically-active agent is selected from the group consisting of vulnerary agents, hemostatic agents, antibiotics, antihelminthics, anti-fungal agents, hormones, anti-inflammatory agents, polypeptides, oligonucleotides, cytokines, antibodies, and enzymes.

11. A hydrogel synthesized with the method of claim 1.

12. A wound dressing comprising the hydrogel of claim 11.

13. A method of treating a wound in a subject comprising applying to the wound the hydrogel of claim 11.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Linker

<400> SEQUENCE: 1

Gly Gly Gly Ser
1

<210> SEQ ID NO 2
<211> LENGTH: 5
<212> TYPE: PRT
<213> ORGANISM: Artificial Sequence
<220> FEATURE:
<223> OTHER INFORMATION: Therapeutic peptide

<400> SEQUENCE: 2

Trp Asn Ser Thr Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Therapeutic peptide

<400> SEQUENCE: 3

Asn Gln His Thr Pro Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Therapeutic peptide

<400> SEQUENCE: 4

Val Ser Asn Gln His
1               5

<210> SEQ ID NO 5
<211> LENGTH: 6
<212> TYPE: PRT
<213> ORGANISM: Artificial Sequence
<220> FEATURE:
<223> OTHER INFORMATION: Therapeutic peptide

<400> SEQUENCE: 5

Val Gln Ala Thr Gln Ser
1               5
```